(12) United States Patent
Hanson et al.

(10) Patent No.: US 10,834,932 B2
(45) Date of Patent: *Nov. 17, 2020

(54) SYSTEM FOR MEASURING SMOKE ABSORPTION INTO FOOD PRODUCTS AND METHOD OF MAKING THE SYSTEM

(71) Applicant: Sugar Creek Packing Co., Washington Court House, OH (US)

(72) Inventors: Robert E. Hanson, Hudson, WI (US); David Martin Phinney, Columbus, OH (US); Joelle Hemmelgarn, Coldwater, OH (US); Jacquelyn Blanchard, Cincinnati, OH (US); Matthew Wesley, Evansville, IN (US); Matthew Tripp, West Chester, OH (US); Alex Gutkoski, Blacklick, OH (US); Mitch Wiles, Valparaiso, IN (US)

(73) Assignee: SUGAR CREEK PACKING CO., Washington Court House, OH (US)

( * ) Notice: Subject to any disclaimer, the term of this patent is extended or adjusted under 35 U.S.C. 154(b) by 223 days.

This patent is subject to a terminal disclaimer.

(21) Appl. No.: 15/948,513

(22) Filed: Apr. 9, 2018

(65) Prior Publication Data

US 2019/0307139 A1 Oct. 10, 2019

(51) Int. Cl.
*G01N 33/00* (2006.01)
*A23B 4/052* (2006.01)
(Continued)

(52) U.S. Cl.
CPC ........... *A23B 4/052* (2013.01); *G01N 33/025* (2013.01); *G01N 33/04* (2013.01); *G01N 33/12* (2013.01); *A23V 2002/00* (2013.01)

(58) Field of Classification Search
CPC ....... A23B 4/052; G01N 33/025; G01N 33/04
See application file for complete search history.

(56) References Cited

U.S. PATENT DOCUMENTS 3,943,841 A 3/1976 Huang
4,558,196 A * 12/1985 Babasade ............... H05B 6/108
219/629

(Continued)

FOREIGN PATENT DOCUMENTS

CN 206177874 5/2017

OTHER PUBLICATIONS

PCT, International Search Report and Written Opinion, International Application No. PCT/US2019/026296 (dated Jun. 26, 2019).

(Continued)

*Primary Examiner* — Alvaro E Fortich
(74) *Attorney, Agent, or Firm* — Thompson Hine LLP

(57) ABSTRACT

A system for measuring smoke absorption into food products includes a surrogate that reacts to a presence of smoke in air ambient to the surrogate and the food products; and the surrogate is configured to change a state after an exposure to the smoke for a time sufficient to effect a predetermined amount of smoke absorption by a selected food product. A method of making the system for measuring smoke absorption into food products includes placing the surrogate in air ambient to the surrogate in a smokehouse where the food products are to be smoked, configuring the surrogate to change a state after an exposure to the smoke for a time sufficient to effect a predetermined amount of smoke absorption by the food products; and measuring the change of state of the surrogate.

22 Claims, 3 Drawing Sheets

(51) Int. Cl.
*G01N 33/02* (2006.01)
*G01N 33/04* (2006.01)
*G01N 33/12* (2006.01)

(56) References Cited

U.S. PATENT DOCUMENTS

| | | | | |
|---|---|---|---|---|
| 5,459,078 | A * | 10/1995 | Kline | G01N 33/532 |
| | | | | 436/518 |
| 7,036,452 | B1 * | 5/2006 | Tester | G01K 3/04 |
| | | | | 116/206 |
| 8,080,268 | B2 | 12/2011 | Wilfer et al. | |
| 9,408,403 | B2 | 8/2016 | Joly et al. | |
| 2003/0045608 | A1 | 3/2003 | Ochiai et al. | |
| 2004/0146610 | A1 * | 7/2004 | Lee | C08K 5/103 |
| | | | | 426/99 |
| 2005/0222778 | A1 * | 10/2005 | Levinson | G06Q 50/04 |
| | | | | 702/19 |
| 2006/0188615 | A1 * | 8/2006 | Wilfer | A22C 13/0013 |
| | | | | 426/138 |
| 2008/0182035 | A1 * | 7/2008 | Samuels | A22C 13/0013 |
| | | | | 427/540 |
| 2009/0118175 | A1 * | 5/2009 | Macina | C12Q 1/6886 |
| | | | | 514/1.1 |
| 2009/0314066 | A1 * | 12/2009 | Nieuwenhuis | G01N 15/0656 |
| | | | | 73/61.71 |
| 2012/0093984 | A1 * | 4/2012 | Haus, Jr. | A23L 13/72 |
| | | | | 426/140 |
| 2014/0023756 | A1 * | 1/2014 | Joly | A23B 4/044 |
| | | | | 426/231 |
| 2014/0210127 | A1 | 7/2014 | Sebastian | |
| 2015/0030728 | A1 * | 1/2015 | Raghavan | A47J 27/04 |
| | | | | 426/231 |

OTHER PUBLICATIONS

English translation of CN 206177874 (published May 17, 2017).

* cited by examiner

SYSTEM FOR MEASURING SMOKE ABSORPTION INTO FOOD PRODUCTS AND METHOD OF MAKING THE SYSTEM

TECHNICAL FIELD

This disclosure relates to food preparation systems and processes, and more particularly, to systems and processes for imparting a smoke flavor to food products.

BACKGROUND

A goal of commercial food preparation systems and processes is to produce a food product that is consistently of high quality in a minimal amount of preparation time. Such systems and processes must produce high quality food products whose taste, texture, and appearance consistently falls within a desired range, and which minimizes rejects. Achieving such consistency in commercial food product preparation is particularly difficult when smoking food products. This is particularly difficult when smoking animal protein, because the rate of smoke absorption varies with the type and cut of animal protein.

With most smoking processes, the food product to be smoked is placed in an enclosed chamber called a smokehouse. The food product may be placed on racks or hangers within the smokehouse, or pass through the smokehouse on a conveyor. The air in the smokehouse is charged with smoke from a smoke generator. The smoke generator may generate smoke by smoldering or burning wood, which may be selected from hickory, mesquite, cherry, beech wood, pecan wood, apple wood, and oak.

The smoke generator may be located outside the smokehouse, in which case the generated smoke is blown into the smokehouse through a duct. In other designs, the smoke generator may be integrated with the smokehouse. Most smokehouses also include an exhaust vent that may be powered and operate together with the smoke generator to regulate the smoke density in the air within the smokehouse. Smokehouses also may include a regulated heating system to maintain the temperature within the smokehouse within a desired range, and a humidifier to regulate humidity.

Factors including smoke density, temperature, food product residence time within the smokehouse, the type of food product being smoked, and the desired level of smoke absorption must be controlled to produce the desired level of smoke flavor in the food product. Typically, these factors are controlled by an experienced operator who relies on their skill at setting these operating parameters of the smokehouse. Such subjective setting and control can lead to inconsistent levels of smoke flavor absorbed by the food product between batches or runs, and between food product smokehouse facilities.

Attempts have been made to provide smokehouse operation that utilizes objective measurement techniques. In one example, sample smoke products are ground to make a slurry and their pH is measured to determine whether a desired level of smoke is absorbed by the smoked food product. Because smoke is acidic, an increase in the pH of a food product is indicative of an amount of smoke absorbed. A disadvantage with such a process is that it requires the continual destruction of the selected food product being smoked to monitor the progression of smoke absorption, and to determine when a desired amount of smoke absorption by the food product has occurred. This destructive testing creates food product waste that adds to the production cost of the smoking operation. Further, if the tested food product indicates that too much smoke has been absorbed by a batch or a run, the remaining food product of the run must be degraded as second-rate product or rejected as waste.

Accordingly, there is a need for a system and method for measuring smoke absorption into food products that does not require destructive testing of the food products, and that relies on objective measurements to promote consistency. There is also a need for a system and method for measuring smoke absorption into food products that operates and can be monitored in real time during the smoking operation, thereby optimizing the time required to achieve a desired amount of smoke absorption into the food product.

SUMMARY

The present disclosure is a system and method for measuring smoke absorption into a food product, and a method for making the system. The system and method provide an objective determination of smoke absorption into a food product, thereby providing consistency and uniformity to the smoked food product produced, without testing the food product itself. In exemplary embodiments, the disclosed system and method for measuring smoke absorption determines the amount of smoke absorbed into a food product in real time, which minimizes the likelihood of downgraded or rejected products due either to inadequate or excessive smoke absorption.

In an exemplary embodiment, a system for measuring smoke absorption into food products includes a surrogate that reacts to a presence of smoke in air ambient to the surrogate. The surrogate is configured to change a state thereof after an exposure to the smoke for a time sufficient to effect a predetermined amount of smoke absorption by a selected food product exposed to the smoke in the air ambient to the surrogate.

In another exemplary embodiment, a system for measuring smoke absorption into food products includes a surrogate that reacts to a presence of smoke in air ambient to the surrogate and to the food products, the surrogate including a casing made of a semipermeable membrane and containing water; a conductivity meter having a probe positioned in the water within the casing to measure electrical conductivity of the water, wherein the electrical conductivity of the water in the casing increases as the smoke in the air ambient to the surrogate is absorbed through the semipermeable membrane and diffuses in the water, and as the smoke in the air ambient to the surrogate is absorbed into the food products; and a control that generates a signal and/or a display indicative of a selected electrical conductivity of the water that corresponds to a selected amount of smoke absorption by the food products exposed to the smoke in the air ambient to the surrogate.

In yet another exemplary embodiment, a method of making a system for measuring smoke absorption into food products includes placing a surrogate that reacts to a presence of smoke in air ambient to the surrogate in a smokehouse where the food products are to be smoked, the surrogate is configured to change a state thereof after an exposure to the smoke for a time sufficient to effect a predetermined amount of smoke absorption by a selected food product exposed to the smoke in the air ambient to the surrogate; and placing a probe of a sensor in the surrogate to measure a degree of the change of state of the surrogate, the sensor calibrated to indicate a selected degree of the change of state corresponding to a selected amount of smoke to be absorbed by the food products.

In still another exemplary embodiment, a method for measuring smoke absorption into food products includes placing a surrogate that reacts to a presence of smoke in air ambient to the surrogate in the presence of the food products; and observing a change a state of the surrogate after an exposure to the smoke for a time sufficient to effect a predetermined amount of smoke absorption by the food products exposed to the smoke in the air ambient to the surrogate.

Other objects and advantages of the disclosed system for measuring smoke absorption into food products and method of making the system will be apparent from the following description, the accompanying drawings, and the appended claims.

DETAILED DESCRIPTION

In an exemplary embodiment, the disclosed system for measuring the amount of smoke absorbed into a food product. As used herein the term "food product" or "food products" includes any food or food ingredient for human consumption, and includes meats, in particular pork bellies, fish, cheeses, sausages and other prepared meats, spices, vegetables, in particular root vegetables, fruits, nuts, and food ingredients. The disclosed system utilizes a surrogate, which is not itself the food product, nor is it derived from or taken from the food product that is smoked. Instead, the surrogate contains a substance that reacts to the chemical properties of smoke. Smoke is mixture of different compounds dissolved or carried in air. It has been determined that acidic compounds make up approximately 96% of the smoke composition. Without being held to any particular theory, it is generally accepted that smoke is absorbed into a food product, such as a protein, by dissolving itself in water contained in the protein. As the protein cooks, the moisture is driven off, leaving the smoke compounds behind that are responsible for flavor and color changes to the food product.

Accordingly, in an exemplary embodiment described herein, the system utilizes a surrogate, such as water, in particular distilled or deionized water, as a suitable substitute to determine the amount of smoke absorbed into a food product, such as a moisture-laden protein, in particular a pork belly, while in a smokehouse. During the smoking process, the surrogate is tested to determine the rate of smoke absorption by the surrogate, which is indicative of the rate of smoke absorption into the food product.

The relation between the rate of smoke absorption into the surrogate and the rate of smoke absorption into the food product is determined by experimentation. A change of the state of the surrogate caused by absorption of smoke into the surrogate, which may take the form of a change in pH of the water in the surrogate to a preselected level of acidity, and/or a change in electrical conductivity of the water in the surrogate to a preselected conductivity, is measured continuously during the smoking process. When the target pH and/or conductivity of the water in the surrogate is reached, the smoking process is completed for the food products in the smokehouse.

Figure 1:
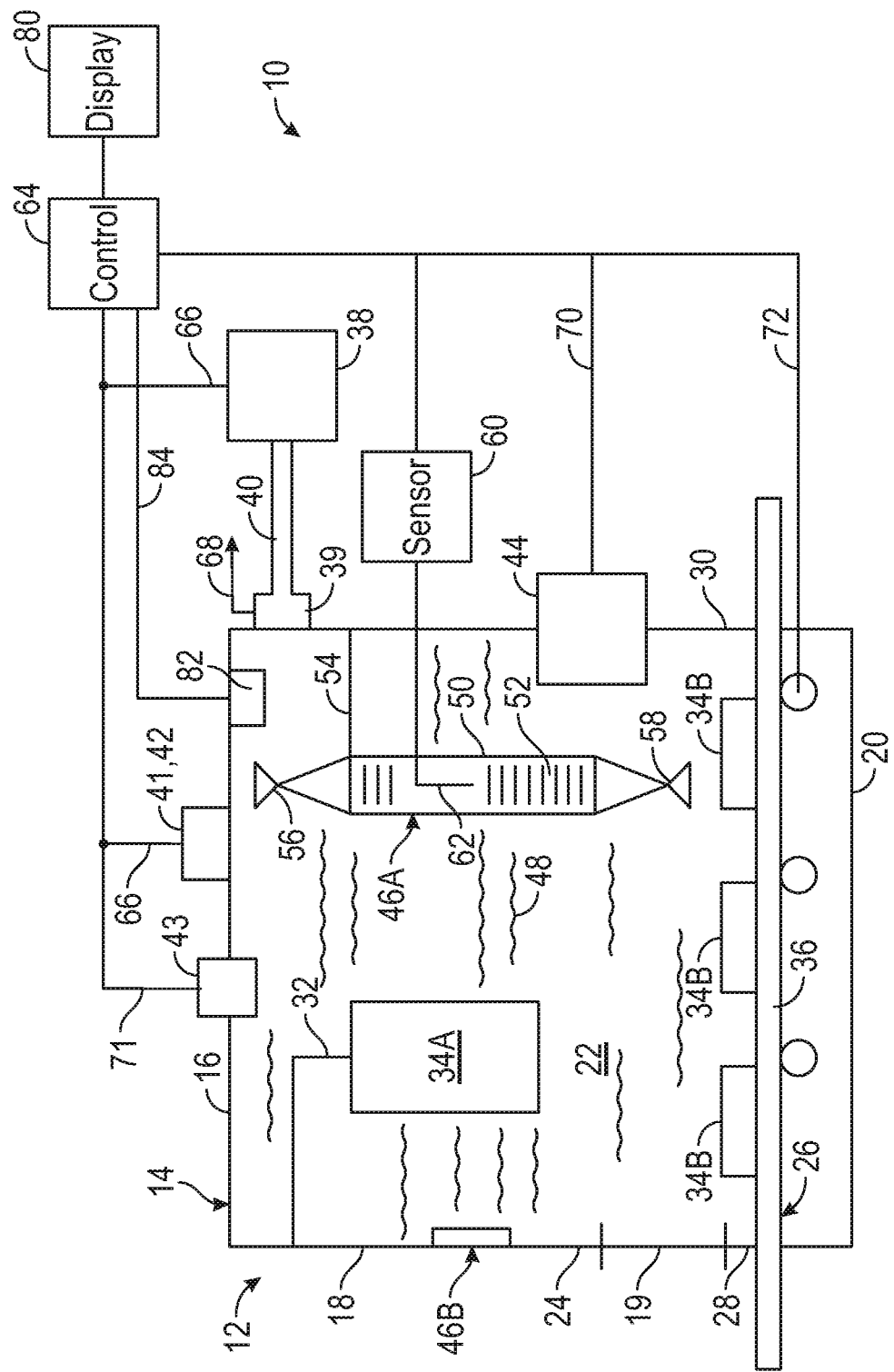
FIG. 1 is a schematic side elevation of a smokehouse incorporating an exemplary embodiment of the disclosed system for measuring smoke absorption into food products.

As shown in FIG. 1, an exemplary embodiment of the system for measuring smoke absorption into food products, generally designated 10, is used with, or incorporated into, a smokehouse, generally designated 12. The smokehouse 12 typically is an enclosed room 14 with a top wall 16, four side walls 18, and a floor 20 defining an interior 22. One of the side walls 18, or an access door 19 in the wall, includes an inspection window 24 that allows an operator to view the interior 22. The access door 19 (there may be two, but only one is shown) enables an operator to enter to load and remove food products to be smoked. In an exemplary embodiment, the smokehouse 12 includes a conveyor 26 that passes through openings 28, 30 in the walls 18.

As an alternative to the conveyor 26, or in addition to the conveyor, the smokehouse 12 includes a rack system 32 for hanging food product 34A in the interior. The conveyor 26 includes a belt 36 that supports food product 34B and conveys it through the interior 22. The smokehouse 12 includes a smoke generator 38 that is connected to the interior 22 by a conduit 40 and includes a smoke generator fan 39 for blowing or drawing smoke into the interior 22 of the smokehouse 12. In embodiments, the enclosed room 14 includes an intake vent 41 that may include an intake fan, combined with an exhaust vent 42 that may include an exhaust fan. The smokehouse 12 may include a humidification valve 43 that allows steam and/or water mist into the interior 22 to regulate the humidity of the interior. The intake and exhaust vents 41, 42, respectively, are actuated in cooperation with the smoke generator 38 and smoke generator fan 39 to control the density of smoke in the interior 22. In exemplary embodiments, the smoke generator 38 generates smoke by burning or smoldering a selected combustible material, such as wood, in particular hickory, mesquite, apple wood, oak, cherry, beech wood, pecan wood, and/or ash. The wood itself may be flavored with spices, essential oils, herbs, or spirits, such as bourbon.

The smoke generator fan 39 can be set to blow smoke into the interior 22 of the room 14 at selected flow rates, and the intake vent 41 and/or exhaust vent 42 can be adjusted to vary flow rates as well. The smokehouse 12 also may include a heater 44 for heating the interior. Both the fan powering the exhaust vent 42 and the heater 44 may be adjusted to vary the exhaust flow rate and the rate of heat input to the interior 22, respectively. The fan of the intake vent 41 is actuated to draw fresh air ambient to the exterior of the smokehouse, and the smoke generator fan 39 draws or blows smoke into the smokehouse 12. In embodiments, the smokehouse 12 also includes a thermometer and/or a thermostat, which may be incorporated into the heater 44, as well as a humidity sensor that may be incorporated into the humidification valve 43.

The system 10 includes a surrogate 46A that reacts to a presence of smoke 48 in air ambient to the surrogate, namely, in the interior 22 of the smokehouse 12. The surrogate 46A is configured to change state after an exposure to the smoke 48 for a time sufficient to effect a predetermined amount of smoke absorption by a selected food product 34A and/or 34B exposed to the smoke in the air ambient to the surrogate. The surrogate is not the food product 34A, 34B in the smokehouse 12, and is not derived from the food product in the smokehouse. The surrogate 46A is selected from a liquid and a gel, and the change of state is a change in a state of the liquid or the gel. In an exemplary embodiment, the change in state is a change in electrical conductivity to a preselected degree of electrical conductivity of the liquid or gel. In another exemplary embodiment, the change in state of the surrogate 46A is a change in pH of the liquid or the gel to a preselected pH value.

In the embodiment shown in FIG. 1, the surrogate 46A includes a casing 50 made of a semi-permeable membrane that permits absorption of smoke 48 from ambient air in the interior 22 of the smokehouse In embodiments, the semi-permeable membrane casing 50 is made of material selected from animal intestine, cellulose, collagen, fibrous cellulose, and a polymer, all of which are permeable to smoke particles and gases, but impermeable to the liquid or the gel contained in the semipermeable membrane of the casing, except through evaporation of the liquid as water vapor. In an exemplary embodiment, the casing 50 is cylindrical or tubular in shape and is tied or otherwise attached to and suspended downwardly from a bracket 54 that is mounted on a wall 18 of the smokehouse 12.

In a particular embodiment, the surrogate 46A is a 4-foot length of casing 50 that is tied off at its opposing ends 56, 58 and is suspended vertically within the interior 22. The casing 50 contains a liquid 52 that is retained in its interior. In an embodiment, the liquid 52 is water, and in particular deionized or distilled water. The system 10 also includes sensor 60 that may take the form of an electrical conductivity meter or a pH meter. The sensor 60 includes, or is connected to receive a signal from, a probe 62 that is mounted in the liquid 52 within the casing 50. In embodiments, the probe 62 is connected by wire or wirelessly to the sensor 60.

In an exemplary embodiment, the system 10 includes a control 64 that is connected to receive a signal from the sensor 60, which may be an electrical conductivity meter or the pH meter, indicative of the electrical conductivity or a pH of the liquid 52. The control 64 may receive a signal directly from the probe 62, by wire or wirelessly, if the sensor 60 is incorporated in the control. The control 64 is programmed to compare the conductivity or pH measured by the sensor 60 and probe 62 to a selected or desired target conductivity or pH for the selected food product 34A and/or 34B. This selected or desired conductivity or pH is developed by conducting tests on various food products, in which a particular food product is tested using varied settings of smoke density, temperature, and residence time within the interior 22 of the smokehouse 12.

The control 64 is connected to the smoke generator 38, and intake vent 41 and exhaust vent 42 by cable 66, smoke generator fan 39 by cable 68, heater 44 by cable 70, humidification valve 43 by cable 71, and conveyor 26 by cable 72. In embodiments, these communication and control connections are wired or wireless and/or part of a network, such as a neural network. In an embodiment, the system 10 includes a smoke detector 82, connected to the control 64 wirelessly or by a cable 84, and may be part of a network. The smoke detector 82 measures the density of the smoke 48 in the interior 22. The smoke detector is mounted inside the enclosed room 14 of the smokehouse 12 to sample the density of the smoke 48 in the interior 22. An example of a suitable smoke detector 82 is an MQ-2 gas sensor interfaced with an Arduino board, which outputs a reading in parts per million of smoke in the air that is conveyed to the control 64. The Arduino board may be separate from or incorporated into the control 64. The control 64 is programmed to actuate the smoke generator 38 to maintain a selected smoke density in the interior 22.

In an exemplary embodiment, the control 64 is programmed to send an actuation signal to regulate the function of one or more of the smoke generator 38, the fan of intake vent 41 and fan of exhaust vent 42, which may act in tandem, the heater 44, the smoke generator fan 39, and the conveyor 26 in the smokehouse 12 containing the surrogate 46A and the food products 34A and/or 34B to obtain the measured conductivity or pH in a selected range after a selected time interval of residence in the smokehouse interior. In the case of the smoke generator 38, the control 64 can actuate the smoke generator fan 39 to increase or decrease the amount of smoke 48 generated and entering the interior 22 and vary the flow rate of the intake vent 41 and/or exhaust vent 42 fan. With the heater 44, the control 64 can increase or decrease the amount of heat generated and blown or radiated into the interior 22, and the control can increase or decrease the speed of the conveyor 26, thereby increasing or decreasing the residence time of the food products 34B in the interior 22 and consequent exposure to smoke 48.

Figure 2:
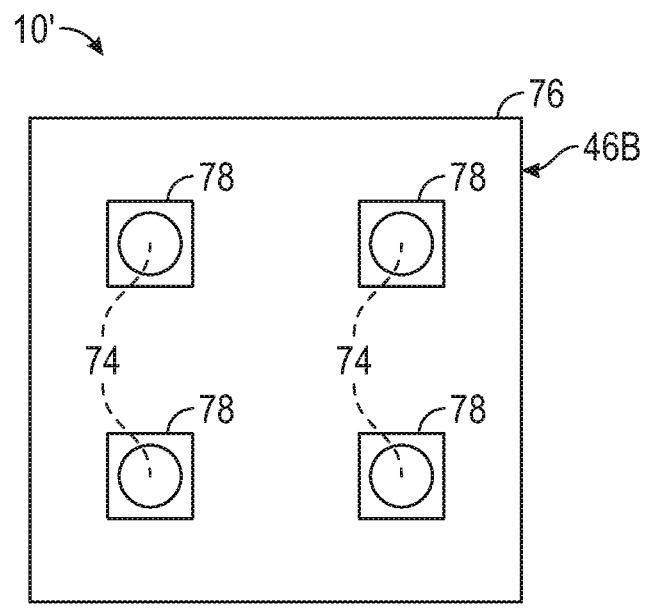
FIG. 2 is a schematic top plan view of another exemplary embodiment of the disclosed system for measuring smoke absorption into food products.

As shown in FIGS. 1 and 2, in another exemplary embodiment, the system 10' includes a surrogate 46B. The surrogate 46B is a disk 74, or multiple disks 74, of pH indicator applied to a substrate 76. The disks 74 may be in solid, liquid, or paste form. The disks 74 of pH indicator are covered by a smoke-permeable gel layer 78, which, in an exemplary embodiment is a whey protein gel layer. Also in embodiments, the pH indicator is phenolphthalein. The substrate 76 may be a polymer, such as nylon, glass, sized paper, cardstock, or a clear polymer, such as polyethylene terephthalate, an acrylic, or a polycarbonate.

The surrogate 46B is attached to the inside of the inspection window 24 of the smokehouse 12, by a releasable adhesive or suction cups (not shown) or hung from a hook, or placed in the interior 22 where the disks 74 of pH indicators can be seen visually through the inspection window 24 by an operator. The thickness of the gel layer 78 is selected to permit penetration of the smoke 48 to the disks 74 at a selected rate that corresponds to a desired or a selected penetration rate of smoke into the food product 34A, 34B. The pH indicators of the disks 74 react when contacted with the acidic smoke that has penetrated the gel layer 78 and change color. The color change is a change in state of the surrogate 46B that indicates that a sufficient amount of smoke has absorbed into the food product 34A, 34B.

In another exemplary embodiment, shown in FIG. 1, the system 10 for measuring smoke absorption into food products 34A, 34B includes a surrogate 46A, which is not the food product, that absorbs smoke 48 in air within the smokehouse 12 ambient to the surrogate and to the food products and in response changes state. The surrogate 46A includes a casing 50 made of a semipermeable membrane. The casing 50 contains a liquid 52, which in embodiments is water, in particular distilled water and/or deionized water. Distilled and/or deionized water is not only pH neutral, but has little or no electrical conductivity.

A sensor 60 in the form of an electrical conductivity meter has a probe 62 that is positioned in the liquid 52 within the casing 50 to measure electrical conductivity of the liquid. The electrical conductivity of the liquid 52 in the casing 50 increases as the smoke 48 in the air ambient to the surrogate 46A penetrates the semipermeable membrane casing 50 and diffuses in the water, and as the smoke in the air ambient to the surrogate is absorbed into the food products 34A, 34B.

A control 64 generates a signal, which may take the form of an audible and/or visual alarm incorporated in the control, and/or a screen display on a display 80, indicating that a selected level of electrical conductivity of the liquid 52 has been reached that corresponds to a selected or desired amount of smoke absorption by the food products 34A, 34B exposed to the smoke 48 in the air ambient to the surrogate within the room 14 of the smokehouse 12. Alternatively, or in addition, the display 80 can receive a signal from the control 64 to show a real time pH and/or conductivity number readout and/or a graph showing cumulative absorption of smoke by the surrogate 46A. In embodiments, the control 64 includes a data store, which may be remote, to store all readings of the sensor, paired with a time stamp and SKU (stock keeping unit) of the food products, smoke density read by smoke detector 82, and other variables including smoke temperature, meat temperatures, wet bulb and dry bulb temperature, relative humidity, and food product residence time, for later reference.

The control 64 is adapted to regulate the function of one or more of the smoke generator 38 of the smokehouse 12 containing the surrogate 46A and the food products 34A, 34B, the intake vent 41 and exhaust vent 42, the humidification valve 43, the smoke generator fan 39, the conveyor 26, and the heater 44 and heater fan. In the embodiments disclosed herein, the food product 34A, 34B is selected from meats, in particular pork bellies, fish, cheeses, sausages and other prepared meats, spices, vegetables, in particular root vegetables, fruits, nuts, and food ingredients.

Figure 3:
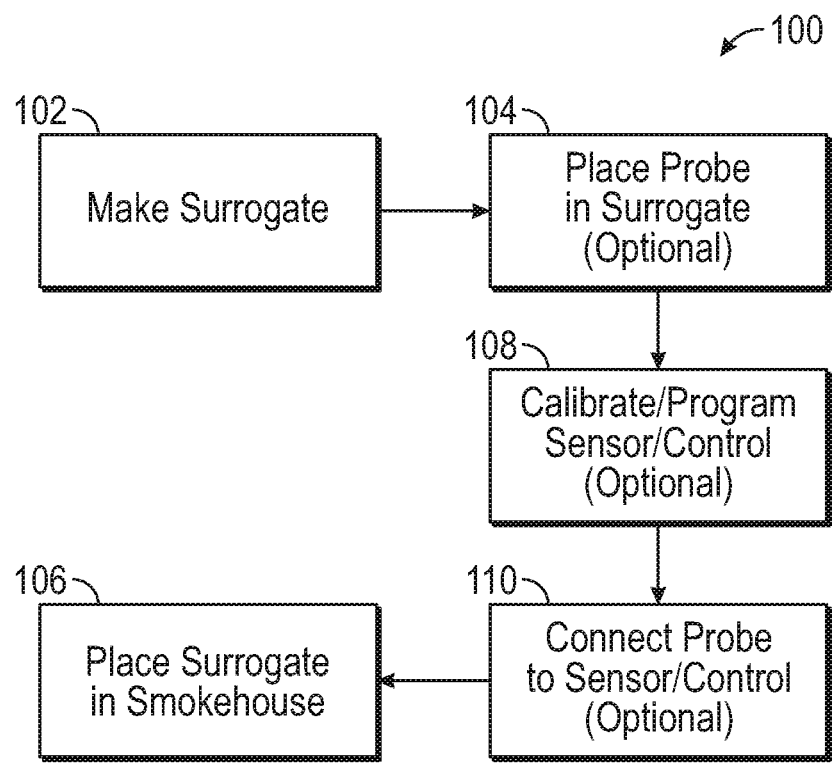
FIG. 3 is a flow chart showing an exemplary embodiment of the method for making the disclosed system for measuring smoke absorption into food products.

As shown in FIG. 3, a method 100 of making the system 10, 10' for measuring smoke absorption into food products 34A, 34B begins with making the surrogate 46A, 46B, as indicated by block 102. In the embodiment shown in FIG. 1, as indicated in block 104, making the surrogate 46A includes taking a casing 50 made of a semipermeable membrane, filling it with liquid or gel 52, placing a probe 62 in the liquid or gel within the casing, and sealing the opposing ends 56, 58 of the casing to retain the liquid or gel and probe therein. In embodiments, a liquid 52 is used and is water, in particular distilled water or deionized water.

In the embodiment shown in FIG. 2, the surrogate 46B is made by attaching the disks 74, which may be of any shape in addition to round, of a pH indicator to a substrate 76, and covering the disks with the smoke-permeable gel layer 78.

As indicated in block 106, with the embodiments of 10 and 10', the surrogate 46A, 46B is placed in the interior 22 of the smokehouse 12, where it will be exposed to smoke 48 in air ambient to the surrogate where the food products 34A, 34B are to be smoked. With each embodiment of the system 10, 10', the surrogate 46A, 46B is configured to change its state after an exposure to the smoke 48 for a time sufficient to effect a predetermined amount of smoke absorption into the selected food product 34A, 34B exposed to the smoke in the air ambient to the surrogate.

As indicated in block 108, before or after placing the probe 62 of the sensor 60 in the surrogate 46A to measure a degree of the change of state of the surrogate, the sensor is calibrated or programmed to indicate a selected degree of the change of state corresponding to a selected amount of smoke 48 to be absorbed by the food products 34A, 34B. This calibration or programming utilizes data gathered empirically, recording smoke density, air temperatures, humidity, and residence time for various types and forms of food products 34A, 34B from previously conducted smokehouse 12 operations.

As indicated in block 110, if the system 10 is used, then the sensor 60 is connected to or incorporated in the control 64, and the control is configured to regulate the function of one or more of the smoke generator 38, the smoke generator fan 29, the intake vent 41 and exhaust vent 42, the humidification valve 43, the conveyor 26, and the heater 44 of the smokehouse 12. With the system of FIG. 1, as indicated in block 106, the surrogate 46A is placed in the smokehouse 12, which includes placing the casing 50 made of a semipermeable membrane in the smokehouse after the casing has been filled with the liquid 52, preferably water, and placing the probe 62 in the liquid. Placing the probe 62 of the sensor 60 in the surrogate 46A includes placing the probe in the surrogate to measure the electrical conductivity or the pH of the liquid 52.

Figure 4:
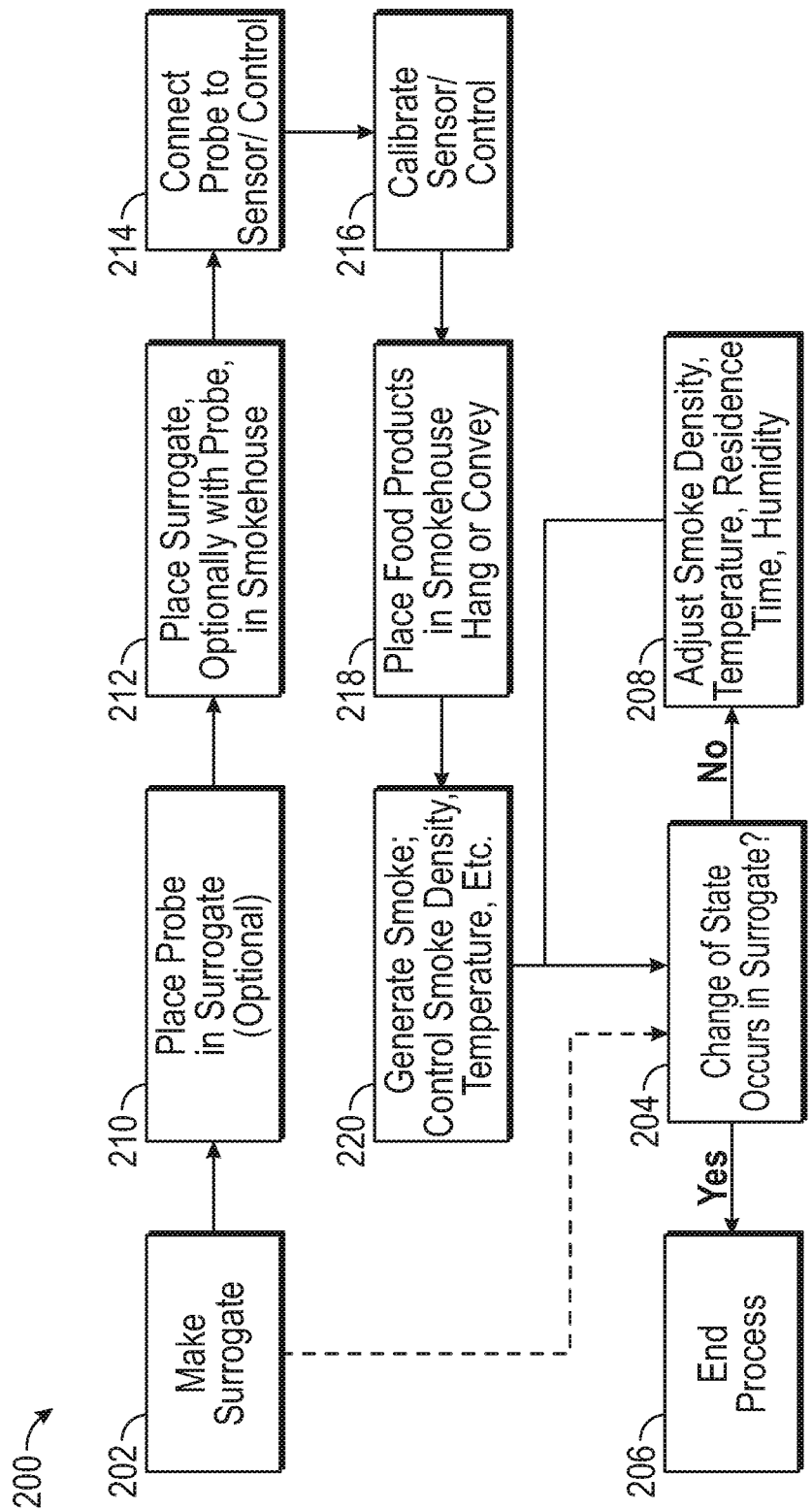
FIG. 4 is a flow chart showing an exemplary embodiment of the method for using the disclosed system for measuring smoke absorption into food products.

As shown in FIG. 4, a method for measuring smoke absorption into food products, generally designated 200, begins by placing the surrogate 46A, 46B that reacts to a presence of smoke 48 in air ambient to the surrogate in the presence of the food products 34A, 34B in the interior 22 of the smokehouse 12, as indicated in block 202. With the surrogate 46B of FIG. 2, the surrogate is mounted within the interior 22 where it can be observed visually through the window 24. The next step is indicated by following dashed line from block 202 to block 204. The food products 34A, 34B are placed or conveyed into the interior 22 of the smokehouse 12, and the smoke generator 38 and smoke generator fan 39 actuated to create and convey smoke 48 into the interior to begin the smoking process. Temperature and humidity may be adjusted by actuating the heater 44 and/or humidification valve 43.

As the smoke 48 penetrates the gel layer 78 to the disks 74 of the surrogate 46B, an operator observes a change of the state of the disks 74 of the surrogate 46B after an exposure to the smoke 48 for a time sufficient to effect a predetermined or desired amount of smoke absorption into the food products 34A, 34B exposed to the smoke in the air ambient to the surrogate in the smokehouse 12. The change of the state of the disks 74 may take the form of a change in color of the disks.

As indicated in block 206, the process ends when the surrogate 46B changes state (i.e., changes color). Optionally, as indicated in block 208, during the process one or more of the food product residence time, smoke density, humidity, and/or air temperature are adjusted to accelerate the smoking process. After the process 200 is completed, the spent surrogate 46B is removed from the smokehouse 12 and replaced with a fresh surrogate 46B to begin the next process or batch.

With the embodiment of FIG. 1, as indicated in block 210, the probe 62 is placed in the liquid or gel 52 of the surrogate 46A. Then, as indicated in block 212, the surrogate 46A, with the probe 62, is placed in the smokehouse 12 with the food products 34A, 34B. The probe 62 is connected to the sensor 60, which may or may not be integral with the control 64, as indicated in block 214. As indicated in block 216, the sensor 60 and/or control 64 is calibrated to a specific one or kind or type of the food product 34A, 34B (which may be specific to the type of food product, its thickness, and cut). The calibration of block 216 may be performed at the beginning of the process, such as at the time of making the surrogate 46A. As indicated in block 218, the food products 34A, 34B are placed in the smokehouse 12, which includes either hanging the food products 34A on rack system 32 or placing them on the belt 36 of the conveyor 26 to be conveyed into the interior 22 of the smokehouse 12.

As indicated in block 220, the smoking process begins when the smoke generator 38 is actuated, which may be effected manually or automatically by the control 64. The control 64 monitors the increase in the pH or the electrical conductivity of the liquid or gel 52 in the casing 50, which indicates a change of state of the surrogate 46A in real time during the food product smoking process, shown in block 204. If necessary, the control 64 adjusts the temperature by actuating the heater 44, and adjusts the density of the smoke 48 by actuating the smoke generator 38, and/or the intake and exhaust vents 41, 42, respectively, and the humidity by actuating the humidification valve 43, as indicated in block 208.

As indicated in block 206, the process 200 ends when the desired pH or degree of electrical conductivity of the liquid or gel 52 is detected by the sensor 60, reading a signal from the probe 62 in the liquid or gel 52 of the surrogate 46A. The desired change of the state of the liquid or gel 52 is transmitted to the control 64, which shuts down the smoke generator 38 and actuates the intake and exhaust vents 41, 42, respectively, to clear the interior 22 of smoke 48 to end the smoking process. The food product 34A, having absorbed the desired amount of smoke, may then be removed from the smokehouse 12. If the conveyor 26 is used, the conveyor is indexed to the next array of food products 34B. The now-spent surrogate 46A (and in the case of the surrogate of FIG. 2, the spent surrogate 46B), is removed from the smokehouse 12 and replaced with a fresh surrogate.

The foregoing systems and methods provide objective, repeatable means for measuring smoke absorption into a wide array of food products. Moreover, the methods and systems are employed in real time, during the smoking process, which minimizes the possibility of oversmoking or undersmoking the food products. This may result in a reduction in the amount of time a food product needs to remain in the smokehouse, and a reduction in the amount of smoke needed to produce the desired color and flavor changes in the food product. Moreover, use of the disclosed systems and methods over time would enable operators to determine the exact levels of desired smoking for many types of food products, and reducing waste due to quality downgrades.

While the forms of apparatus and methods described herein are preferred embodiments of the disclosed system and process for measuring smoke absorption into food products, and method of making, it should be understood that the invention is not limited to these specific systems and processes, and that changes may be made therein without departing from the scope of the invention.

What is claimed is:

1. A system for measuring smoke absorption into a food product, the system comprising:
    a surrogate, which is not itself the food product and the surrogate is not derived from the food product, that reacts to a presence of smoke in air ambient to the surrogate; and
    the surrogate is configured to change a state thereof after an exposure to the smoke for a time sufficient to effect a predetermined amount of absorption of the smoke by a selected food product exposed to the smoke in the air ambient to the surrogate.

2. The system of claim 1, wherein the surrogate is selected from a liquid and a gel layer, and the change of state is a change in the state of the liquid or the gel layer.

3. The system of claim 2, wherein the change of state is a change in electrical conductivity to a preselected degree of electrical conductivity.

4. The system of claim 2, wherein the change of state is a change in pH to a preselected pH value.

5. The system of claim 1, wherein the surrogate is a pH indicator applied to a substrate.

6. The system of claim 5, wherein the pH indicator is covered by a gel layer, in particular a whey protein gel layer.

7. The system of claim 6, wherein the pH indicator is phenolphthalein.

8. The system of claim 1, wherein the surrogate includes a casing made of a semipermeable membrane that permits absorption of smoke from ambient air, the casing containing a liquid or a gel; and the system further comprises an electrical conductivity meter or a pH meter having a probe in the liquid or the gel within the casing that measures an electrical conductivity of the liquid or the gel within the casing.

9. A system for measuring smoke absorption into food products, the system comprising:
    a surrogate that reacts to a presence of smoke in air ambient to the surrogate and to the food products, the surrogate including a casing made of a semipermeable membrane and containing water contained in the casing;
    a conductivity meter having a probe positioned in the water within the casing to measure electrical conductivity of the water, wherein the electrical conductivity of the water in the casing increases as the smoke in the air ambient to the surrogate is absorbed through the semipermeable membrane and diffuses in the water, and as the smoke in the air ambient to the surrogate is absorbed into the food products; and
    a control that generates a signal and/or a display indicative of a selected electrical conductivity of the water that corresponds to a selected amount of smoke absorption by the food products exposed to the smoke in the air ambient to the surrogate.

10. The system of claim 9, wherein the control is adapted to regulate a function of one or more of a smoke generator of a smokehouse containing the surrogate and the food products, an intake fan that draws smoke into the smokehouse, a recirculation fan that recirculates smoke-laden air within the smokehouse, an exhaust vent of a smokehouse containing the surrogate and the food products, a food products conveyor of a smokehouse containing the surrogate and the food products, and a heater of a smokehouse containing the surrogate and the food products.

11. The system of claim 9, wherein the food products are selected from meats, fish, cheeses, sausages, spices, vegetables, and fruits.

12. A method of making a system for measuring smoke absorption into food products, the method comprising:
    placing a surrogate that reacts to a presence of smoke in air ambient to the surrogate in a smokehouse where the food products are to be smoked, the surrogate is configured to change a state thereof after an exposure to the smoke for a time sufficient to effect a predetermined amount of smoke absorption by a selected food product exposed to the smoke in the air ambient to the surrogate; and
    placing a probe of a sensor in the surrogate to measure a degree of the change of state of the surrogate, the sensor calibrated to indicate a selected degree of the change of state corresponding to a selected amount of smoke to be absorbed by the food products.

13. The method of claim 12, further comprising incorporating the sensor in a control; and configuring the control to regulate a function of one or more of a smoke generator of a smokehouse containing the surrogate and the food products, an intake fan that draws smoke into the smokehouse, a recirculation fan that recirculates smoke-laden air within the smokehouse, an exhaust vent of a smokehouse containing the surrogate and the food products, a food products conveyor of a smokehouse containing the surrogate and the food products, and a heater of a smokehouse containing the surrogate and the food products.

14. The method of claim 12, wherein placing the surrogate in a smokehouse includes placing a casing made of a semipermeable membrane in the smokehouse, filling the casing with a liquid, preferably water, and placing the probe in the liquid.

15. The method of claim 14, wherein placing a probe of a sensor in the surrogate includes placing the probe of a sensor in the surrogate to measure conductivity or a pH of the liquid.

16. A method for measuring smoke absorption into food products, the method comprising:
   placing a surrogate that reacts to a presence of smoke in air ambient to the surrogate in a presence of the food products, wherein the surrogate is not itself the food product and is not derived from the food product;
   generating smoke, by a smoke generator, in the presence of the food products and the surrogate;
   observing a change in a state of the surrogate after an exposure to the smoke for a time sufficient to effect a predetermined amount of absorption of the smoke by the food products exposed to the smoke in the air ambient to the surrogate; and
   ending the method by removing the food products from the smoke after the predetermined amount of absorption of the smoke by the food products.

17. The system of claim 16, wherein the semipermeable membrane is selected from animal intestine, cellulose, collagen, fibrous cellulose, and a polymer.

18. The system of claim 16, wherein the liquid is water.

19. A system for measuring smoke absorption into food products, the system comprising:
   a surrogate that reacts to a presence of smoke in air ambient to the surrogate;
   the surrogate is selected to change a state thereof after an exposure to the smoke for a time sufficient to effect a predetermined amount of absorption of the smoke by a selected food product exposed to the smoke;
   the surrogate including a casing made of a semipermeable membrane that permits absorption of the smoke, the casing containing a liquid or a gel; and
   an electrical conductivity meter or a pH meter having a probe in the liquid or the gel within the casing that measures an electrical conductivity of the liquid or the gel within the casing.

20. The system of claim 19, further comprising a control that is connected to receive a signal from the electrical conductivity meter or the pH meter indicative of an electrical conductivity or a pH of the liquid.

21. The system of claim 20, wherein the control is programmed to compare the measured conductivity or pH to a selected conductivity or pH for the selected food product.

22. The system of claim 21, wherein the control is programmed to send an actuation signal to regulate a function of one or more of a smoke generator, an intake fan, a recirculating fan, an exhaust vent, a heater, and a conveyor in a smokehouse containing the surrogate and the food products to obtain a measured conductivity or pH in a selected range after a selected time interval.

* * * * *